United States Patent
Brotz

(10) Patent No.: US 6,620,178 B1
(45) Date of Patent: Sep. 16, 2003

(54) BLOOD VESSEL GRAFTING AID

(76) Inventor: Gregory R. Brotz, P.O. Box 1322, Sheboygan, WI (US) 53081

( * ) Notice: Subject to any disclaimer, the term of this patent is extended or adjusted under 35 U.S.C. 154(b) by 93 days.

(21) Appl. No.: 09/969,488

(22) Filed: Oct. 3, 2001

(51) Int. Cl.$^7$ ............................................. A61B 17/08
(52) U.S. Cl. ...................................................... 606/153
(58) Field of Search ................................. 606/151–158

(56) References Cited

U.S. PATENT DOCUMENTS

| | | | | |
|---|---|---|---|---|
| 5,486,187 A | * | 1/1996 | Schenck | 606/153 |
| 5,549,122 A | * | 8/1996 | Detweilwer | 128/898 |
| 5,755,778 A | * | 5/1998 | Kleshinski | 623/1.13 |
| 6,152,937 A | * | 11/2000 | Peterson et al. | 606/153 |
| 6,187,020 B1 | * | 2/2001 | Zegdi et al. | 606/153 |
| 2001/0001826 A1 | * | 5/2001 | Bolduc et al. | 606/153 |
| 2001/0039425 A1 | * | 11/2001 | Dakov | 606/153 |
| 2001/0047180 A1 | * | 11/2001 | Grudem et al. | 606/153 |
| 2002/0007189 A1 | * | 1/2002 | Yencho et al. | 606/153 |

* cited by examiner

*Primary Examiner*—Michael J. Milano
*Assistant Examiner*—P Roberts
(74) *Attorney, Agent, or Firm*—William Nitkin

(57) ABSTRACT

A blood vessel grafting aid is disclosed for joining two blood vessels together, such grafting aid in one embodiment having a shaft with a centrally positioned plate thereon and a plurality of prongs extending from the shaft to engage into the vessels within the vessels' lumens with the ends of the vessels disposed against the centrally positioned plate which has apertures formed therein which plate, along with the prongs, aids in holding the blood vessels together. The grafting aid dissolves and is absorbed over time, leaving the blood vessels healed together.

10 Claims, 4 Drawing Sheets

BLOOD VESSEL GRAFTING AID

BACKGROUND OF THE INVENTION

1. Field of the Invention

The device of this invention resides in the area of grafting devices to join two blood vessels together during surgery and more particularly relates to a device that fits within the blood vessels' lumens and retains the blood vessels in position in contact with the graft device. During the healing process the blood vessels rejoin and the device dissolves and is absorbed into the body.

2. History of the Prior Art

It is well known that blood vessels can be joined together by stitching and by various grafting techniques.

SUMMARY OF THE INVENTION

It is an object of this invention to provide an improved blood vessel grafting aid which device can join two blood vessels together during surgery. The device is both quick and easy to use and allows for blood flow while the grafting aid is absorbed into the body as the blood vessels heal together. In one embodiment the grafting aid can have a thin shaft formed of a first and second portion with a central position defined therebetween from which first and second portions protrude a plurality of prongs, which extend at an angle toward the central position of the device, on which a plate which can have adhesive thereon is supported by a plurality of support members. The first and second portions of the device disposed on either side of the plate are inserted, respectively, into the lumens of the two blood vessel ends to be joined which ends meet at the plate and are retained in position by the adhesive and by the outwardly extending prongs so that the blood vessel ends can heal and rejoin by the natural healing process. The use of the grafting aid of this invention avoids having to stitch the two blood vessels together which action can be tedious and time-consuming especially when joining many pairs of blood vessels during surgery. Using the grafting device of this invention one can quickly and securely join many pairs of blood vessels which ability is especially useful in treating various types of trauma to the body when fast treatment can be most helpful.

DESCRIPTION OF THE PREFERRED EMBODIMENT(S)

Figure 1:
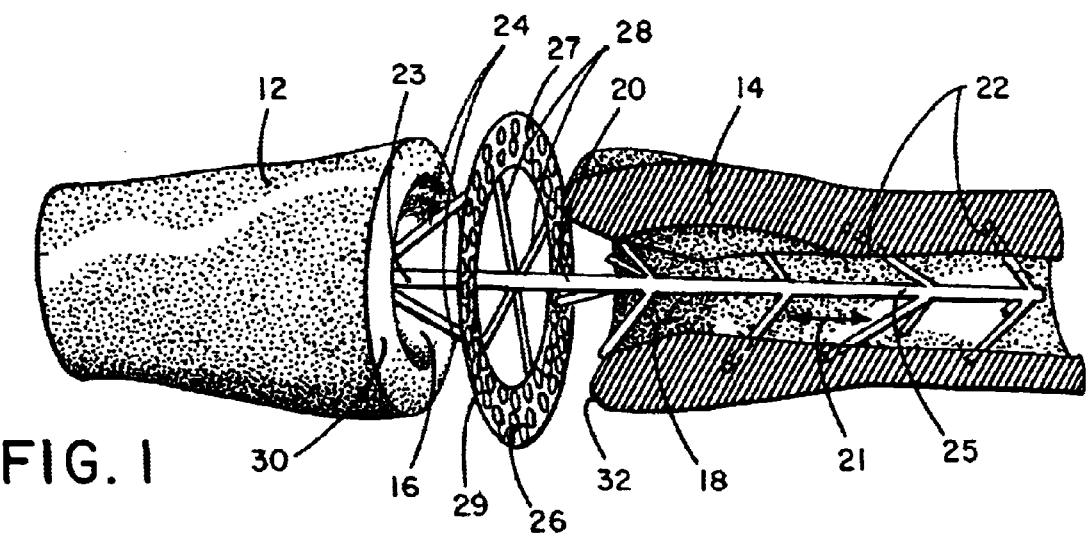
FIG. 1 illustrates a perspective view of the grafting aid of this invention inserted within the lumens of two blood vessels to be joined, showing the plate between the blood vessels and with a portion of one of the blood vessels cut away for viewing the grafting aid of this invention in use.

FIG. 1 illustrates a perspective view of the grafting aid of this invention inserted within the lumens of two blood vessels to be joined. In one embodiment the device of this invention is comprised of first and second portions 23 and 25 of shaft 20 on which are disposed a plurality of first prongs 24 and second prongs 22, respectively. The device of this invention has shaft 20 with a plate 26 centrally positioned perpendicular to the axis 21 of shaft 20 and extending therearound. The ends of the blood vessels, such as first blood vessel end 30 and second blood vessel end 32, are pushed against plate 26 which can have a plurality of apertures formed therein to promote the healing process therethrough in rejoining the blood vessels' ends. In one embodiment adhesive can be disposed on the plate. First and second portions 23 and 25 are inserted, respectively, into the lumens of first blood vessel 12 and second blood vessel 14. The prongs on first and second portions 23 and 25 extend at an angle toward plate 26. Upon insertion, such prongs engage against the insides of the blood vessel lumens to hold the blood vessels open and to prevent shaft 20 from being withdrawn from the blood vessels or the blood vessels from moving rearward off shaft 20. Due to the angle of the prongs they dig into the insides of the blood vessels and prevent the blood vessels from any movement off the device of this invention. Plate 26 can have an adhesive 27 disposed thereon to better retain the ends of first blood vessel end 30 and second blood vessel end 32 together against plate 26. Plate 26 is supported on shaft 20 by plate support members 28 which allow for apertures 29 for blood to pass therethrough once the device of this invention has been inserted into the blood vessel lumens and the blood vessels have been pushed against plate 26. It should be noted that the device of this invention can be made of a bioabsorbable material which will dissolve as first and second blood vessel ends 30 and 32 grow together and interconnect with one another through the natural healing process, leaving the blood vessel intact. Plate 26, shaft 20 and the prongs can all be made of such bioabsorbable materials which are well known in the art. The grafting aids of this invention can be made of materials that are not harmful to the body such as carbohydrates or proteins which can also act as nutrients. Such materials can be selected from types which dissolve at a determined rate for the type of procedure being performed. The materials can be selected from types which accelerate healing and some can even have healing accelerators added to the starting moldable materials from which the grafting aid is formed.

In some embodiments the prongs can be omitted from the shafts if the adhesive system on plate 26 is reliable enough so that instant sealing occurs of blood vessel ends 30 and 32 onto each side of plate 26. In such situations shaft 20 which extends from either side of the centrally positioned plate 26 acts as vessel lumen inserts to position the vessels and aid in maintaining lumen roundness and openness to promote blood flow. Other structures can be utilized to maintain pressure on the vessel ends to urge them against the adhesive plate while such adhesion is occurring. For example, instead of inwardly directed prongs, there can be a plurality of semicircular chevrons scattered in position around the cylindrical or planar structures, as described below, that can be disposed on each side of the adhesive plate.

Figure 2:
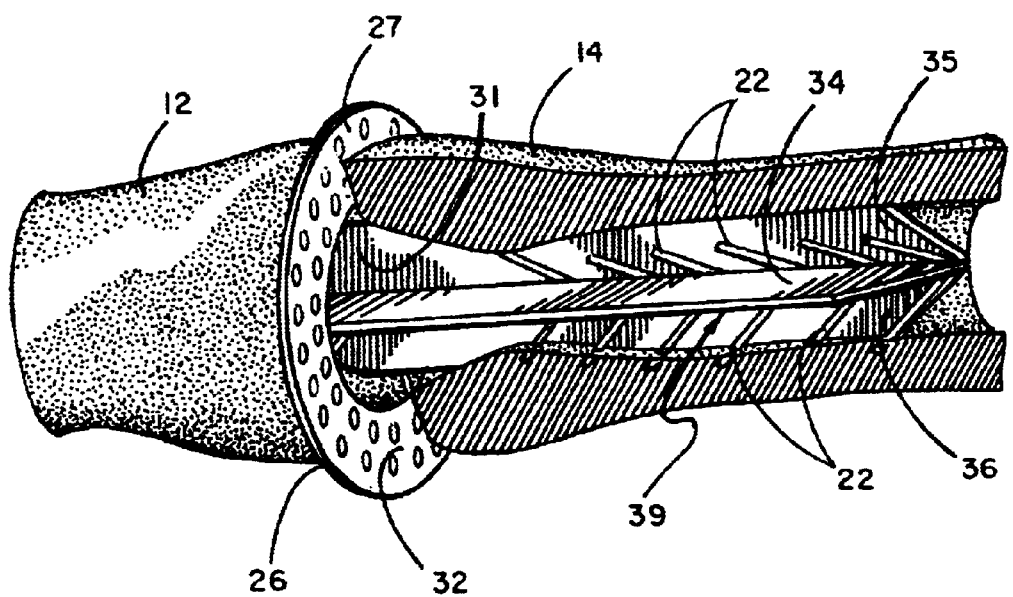
FIG. 2 illustrates a perspective view of an alternate embodiment of this invention in use having a plurality of prongs extending from between a plurality of planar members for holding the lumens of the two blood vessels to be joined in an expanded position to allow the flow of blood therethrough.
Figure 3:
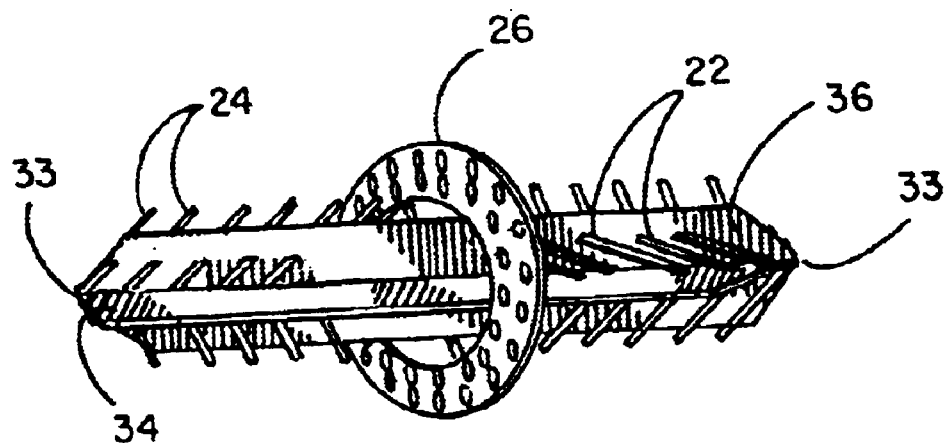
FIG. 3 illustrates a perspective view of the embodiment of FIG. 2 not in use.

In some situations it may be desirable to hold a blood vessel open by more than the outward pressure from a plurality of prongs which might under certain conditions pierce through the blood vessel if the blood vessel wall is not strong enough to prevent such piercing. An alternate embodiment of the grafting aid of this invention is seen in FIG. 2 wherein four planar members are disposed at right angles to one another along the shaft, and second portion 39 is shown extending into second blood vessel 14. Three of the four planar members are seen, being first planar member 34, second planar member 36 and third planar member 35. The insertion end 33, as seen in FIG. 3, of the planar members can be cut at a angle opposite the direction of insertion so as to form a point for ease of entry into the blood vessel lumen. Such pointed ends act as "locators" so as to make it easier to insert the grafting aids into the blood vessel lumens. Between adjacent pairs of planar members can be disposed a plurality of prongs 22 extending at a angle toward plate 26 such that the blood vessel ends, such as second blood vessel end 32, as seen in FIG. 2, can be pushed easily against plate 26 where the adhesive 27 on the plate can be activated such as by salvation of bodily fluids. Many types of adhesives can be utilized such as externally activated adhesives which can be activated by directing high-frequency light thereon, such as ultraviolet light. Other types of adhesives requiring activation can be used. For example, adhesive activation can be accomplished inside the grafting aid packaging by breaking a stored capsule of adhesive catalyst therein, which catalyst can be liquid or gaseous, so that a chemical reaction is started to initiate the catalytic process to activate the adhesive or make the adhesive reactive to bodily fluids or moisture. The activation of the adhesive can also be initiated by dipping the grafting aid into a pool of initiator or by spraying or coating such material on the grafting aid. The embodiment having four planar members disposed at right angles to one another has less tendency for piercing through the wall of the blood vessels since the elongated side edges of the planar members make contact against the blood vessels at 90 degrees with one another, as seen in FIG. 2, and still allows for open spaces 31 therebetween for blood to pass therethrough. Prongs 22 and those not seen in second blood vessel 14 as well as those not seen in first blood vessel 12 on the other side of plate 26 will engage against their respective blood vessels to prevent withdrawal of the grafting aid of this invention once it has been put into position.

Figure 6:
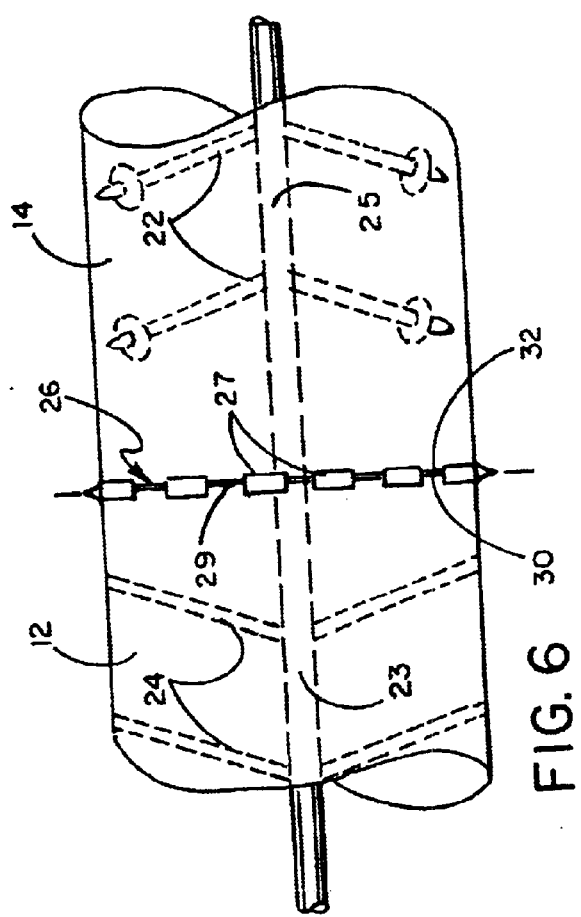
FIG. 6 illustrates a side view of two blood vessels having been joined by the grafting aid of FIG. 1.
Figure 7:
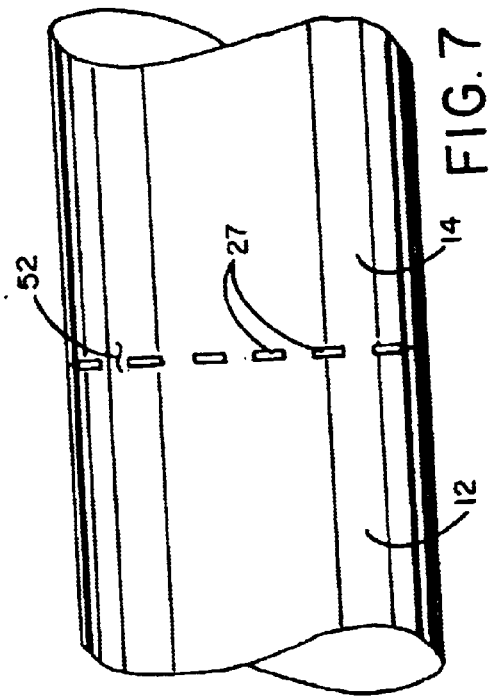
FIG. 7 illustrates the side view of the invention of FIG. 6 showing substantial dissolving and absorbing of the grafting aid.

FIG. 6 illustrates a side view of first and second blood vessels 12 and 14 having been joined against plate 26 wherein portions of the blood vessels meet through apertures 29 and other portions of plate 26 having adhesive 27 thereon to help hold first blood vessel end 30 to second blood vessel end 32. As the grafting aid dissolves, as seen in the side view of FIG. 7, the first and second portions of the grafting aid are absorbed by the body; and the blood vessel grows together initially in the areas, for example area 52, where apertures 29 were located. Adhesive 27 along with the remainder of plate 26 is shown having a substantial portion thereof absorbed which absorption will continue until first and second blood vessels 12 and 14 are entirely rejoined and no portion of the grafting aid remains.

Figure 9:
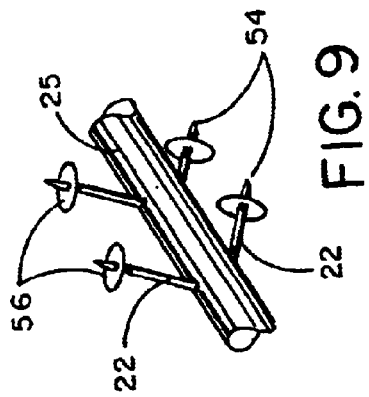
FIG. 9 illustrates a perspective view of a shaft having a plurality of prongs of the type illustrated in FIG. 8.
Figure 8:
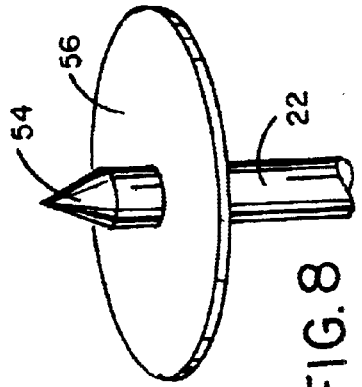
FIG. 8 illustrates a perspective view of an alternate embodiment of an end of a prong.

In some embodiments where the prongs may be thin because of their small size which thinness may increase their likelihood of unintentionally piercing through the blood vessel wall, wider stop members 56, as seen enlarged in FIGS. 8 and 9, can be formed on the ends of the prongs, such as prong 22. The tips 54 of the prongs can be pointed to aid the prongs in digging into and holding against the inside of the blood vessel. FIG. 9 illustrates a plurality of prongs 22 having such piercing preventative ends disposed on a portion of shaft 25.

FIG. 3 illustrates a detailed view of the grafting aid of FIG. 2 when not in use wherein prongs 22 can be seen between first and second planar members 34 and 36 which are positioned at right angles to one another and have generally tapered ends coming to a point 33. The plurality of prongs 22 can be seen aimed back towards plate 26.

Figure 4:
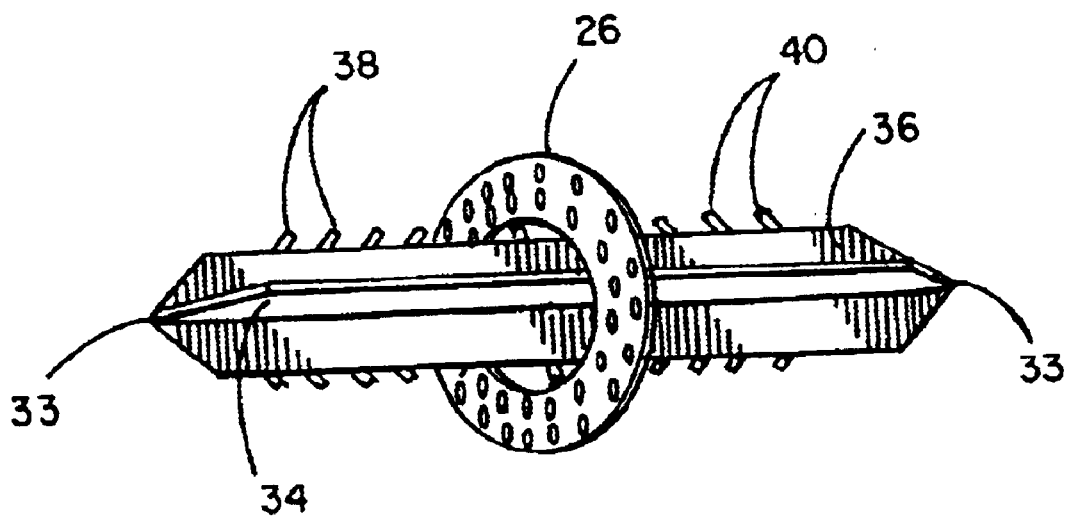
FIG. 4 illustrates an alternate embodiment-of the grafting aid of FIG. 2 wherein the prongs extend not from between the planar members but extend from the side edges of the planar members.

FIG. 4 illustrates a perspective view of an alternate embodiment of the grafting aid of FIGS. 2 and 3 showing first and second planar members 34 and 36 at right angles to one another but not having any prongs disposed from the junctions thereof but having first and second plurality of prong tips 38 and 40 extending at an angle towards plate 26 from side edges 37 of the planar members, such as from planar member 36. It should be noted that such prong tips could also extend from the side edges of first planar member 34 but are not so shown in this view.

Figure 5:
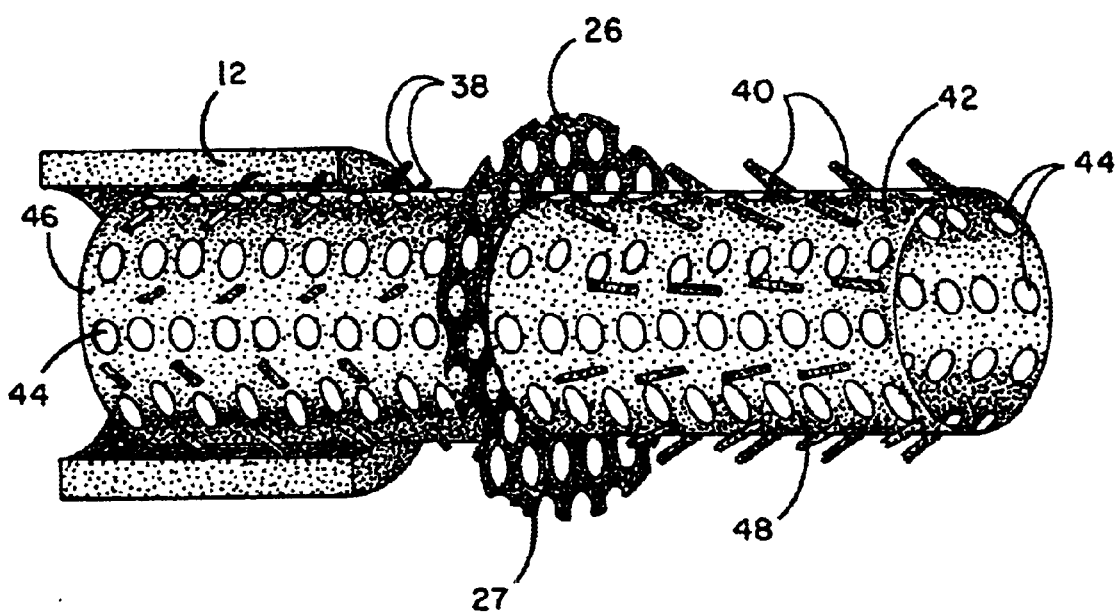
FIG. 5 illustrates a perspective view of an alternate embodiment of this invention wherein the shaft is replaced by a cylindrical member having a plurality of prongs extending therefrom with a plurality of apertures defined in the cylindrical member and in the plate.

In yet another alternate embodiment the grafting aid of this invention the structure supporting the prongs can be cylindrical in nature, as seen in FIG. 5, where cylindrical member 42 is seen bearing a plurality of first prong tips 38 and second prong tips 40 along its length, such prong tips extending at an angle toward plate 26. In this embodiment first portion 46 of cylindrical member 42 is seen inserted into the lumen of first blood vessel 12. A second blood vessel is not illustrated in this view. Once cylindrical member 42 is inserted into the lumens of two blood vessels to be joined, prong tips 38 and 40 dig, respectively, into the inside of the first blood vessel 12 and the second blood vessel, not shown, to prevent withdrawal of cylindrical member 42 therefrom. First portion 46 and second portion 48 of the device are inserted, respectively, into the first and second blood vessels and pushed therein until the ends of the blood vessels meet on either side of plate 26 in which there is seen a plurality of apertures 44 formed therein which allow for the healing process to occur therethrough. Plate 26, as mentioned above, can have adhesive 27 disposed thereon to hold the ends of the blood vessels together during the healing process. Cylindrical member 42, first and second prong tips 38 and 40, and plate 26 can all be composed of bioabsorbable material.

Although the present invention has been described with reference to particular embodiments, it will be apparent to those skilled in the art that variations and modifications can be substituted there for without departing from the principles and spirit of the invention.

I claim:

1. A vein grafting aid for joining two blood vessels together, each blood vessel having an end and a lumen, comprising:

a shaft having a length and an axis extending along its length, said shaft having a first portion, a second portion and a central position defined therebetween;

a plate having a plurality of apertures defined therein, said plate disposed in the area of said central position, said plate disposed perpendicular to said axis of said shaft, said plate extending around said shaft and spaced a distance away from said shaft;

a plurality of plate support members, each having a length and each extending from said central position on said shaft to said plate and defining a plurality of open spaces between said plate, said plate support members and said shaft; and a first and second plurality of prongs extending respectively from said first and second portions of said shaft, said prongs extending at an angle toward said central position such that said shaft and prongs can be inserted into said lumens of said blood vessels wherein said prongs will engage on the inside of said blood vessels such that said ends of said blood vessels can be maneuvered in position against said plate where they will be retained in position by said prongs.

2. The grafting aid of claim 1 further including an adhesive disposed on said plate.

3. The grafting aid of claim 1 further including:

a plurality of planar members each disposed respectively along said first and second portions of said shaft, each planar member having a side edge, said side edges of said planar members for holding said lumens of said first and second blood vessels open; and wherein said plurality of prongs are disposed between adjacent planar members, said prongs for retaining said grafting aid in position in said first and second blood vessels.

4. The grafting aid of claim 2 further including:

a plurality of planar members each disposed respectively along said first and second portions of said shaft, each planar member having a side edge, said side edges of said planar members for holding said lumens of said first and second blood vessels open; and wherein said plurality of prongs are disposed between adjacent planar members, said prongs for retaining said grafting aid in position in said first and second blood vessels.

5. The grafting aid of claim 1 further including:

a plurality of planar members disposed, respectively, along said first and second portions of said shaft, each planar member having a side edge, said side edges of said planar members for holding said lumens of said first and second blood vessels open; and wherein said plurality of prongs extend from said side edges of said planar members.

6. The grafting aid of claim 2 further including:

a plurality of planar members disposed, respectively, along said first and second portions of said shaft, each planar member having a side edge, said side edges of said planar members for holding said lumens of said first and second blood vessels open; and wherein said plurality of prongs extend from said side edges of said planar members.

7. A vein grafting aid for joining two blood vessels together, each blood vessel having an end and a lumen, comprising:

a cylindrical member having a length and an axis defined along said length, said cylindrical member having a first portion, a second portion and a central position defined therebetween along its length, said cylindrical member having a plurality of apertures defined therein;

a plate extending around said cylindrical member at said central position, said plate having apertures defined therein;

a plurality of prong members disposed at an angle on said first and second portions of said cylindrical member directed toward said central position; and said cylindrical member disposed for insertion of said first portion of said cylindrical member into the lumen of the first blood vessel and said second portion of said cylindrical member into the lumen of the second blood vessel, said ends of said blood vessel being respectively pushed against said plate where said blood vessels can grow together through said apertures in said plate and wherein said grafting aid is maintained in position within said first and second blood vessels by said plurality of prong members.

8. The grafting aid of claim 7 further including adhesive disposed on said plate.

9. The grafting aid of claim 7 further including means to prevent said prongs from piercing through said blood vessel.

10. The grafting aid of claim 1 further including means to prevent said prongs from piercing through said blood vessel.

* * * * *